(12) United States Patent
Zhang et al.

(10) Patent No.: US 11,796,710 B2
(45) Date of Patent: Oct. 24, 2023

(54) DETERMINATION OF FORMATION WATER SALINITY USING DOWNHOLE LOW FREQUENCY ELECTROMAGNETIC MEASUREMENTS AND PERMITTIVITY DISPERSIONS BASED THEREON

(71) Applicants: Schlumberger Technology Corporation, Sugar Land, TX (US); Saudi Arabian Oil Company, Dhahran (SA)

(72) Inventors: Ping Zhang, Al-Khobar (SA); Shouxiang Ma, Dhahran (SA); Wael Abdallah, Al-Khobar (SA); Chengbing Liu, Dhahran (SA)

(73) Assignees: SCHLUMBERGER TECHNOLOGY CORPORATION, Sugar Land, TX (US); SAUDI ARABIAN OIL COMPANY, Dhahran (SA)

( * ) Notice: Subject to any disclaimer, the term of this patent is extended or adjusted under 35 U.S.C. 154(b) by 230 days.

(21) Appl. No.: 16/940,479

(22) Filed: Jul. 28, 2020

(65) Prior Publication Data

US 2022/0035066 A1    Feb. 3, 2022

(51) Int. Cl.
| | |
|---|---|
| G01V 3/38 | (2006.01) |
| G01V 3/28 | (2006.01) |
| G01N 33/18 | (2006.01) |
| E21B 49/00 | (2006.01) |
| G01N 27/22 | (2006.01) |
| E21B 49/08 | (2006.01) |
| G01N 33/24 | (2006.01) |

(52) U.S. Cl.
CPC ............. *G01V 3/38* (2013.01); *E21B 49/00* (2013.01); *E21B 49/0875* (2020.05); *G01N 27/221* (2013.01); *G01N 33/18* (2013.01); *G01N 33/24* (2013.01); *G01V 3/28* (2013.01)

(58) Field of Classification Search
None
See application file for complete search history.

(56) References Cited

U.S. PATENT DOCUMENTS

| | | | |
|---|---|---|---|
| 7,501,829 B2 | 3/2009 | Davydychev et al. | |
| 10,208,582 B2 | 2/2019 | Ma et al. | |
| 10,247,849 B2 | 4/2019 | Pfutzner et al. | |
| 2018/0120468 A1* | 5/2018 | Seleznev | G01V 3/20 |
| 2020/0245044 A1* | 7/2020 | Menssen | E21B 47/13 |

OTHER PUBLICATIONS

Clinch, S. et al., "Determining Formation Water Salinity in the Hydrocarbon Leg using Cores and Logs", Petrophysics, 2011, 52(2), pp. 108-123.

(Continued)

*Primary Examiner* — Douglas X Rodriguez
(74) *Attorney, Agent, or Firm* — Ashley E. Brown (57) ABSTRACT

Methods and systems are provided for characterizing formation water salinity of subsurface formation using multi-frequency permittivity data over a range of frequencies below 1 MHz. The multifrequency permittivity data is processed to determine salinity of formation water contained in the subsurface formation. Other useful formation properties (such as formation water saturation) can be determined based on the formation water salinity.

20 Claims, 6 Drawing Sheets

(56) References Cited

OTHER PUBLICATIONS

Ma, S. M. et al., "Resolving the Mixed Salinity Challenges with a Methodology Developed from Pulsed Neutron Capture Gamma Ray Spectral Measurements", SPE 170608, 2014 SPE Annual Technical Conference and Exhibition, Amsterdam, The Netherlands, 12 pages.
Seleznev, N., et al., Coherent interpretation of wideband electromagnetic measurements in the millihertz to gigahertz frequency range, SPWLA 58th Annual Logging Symposium, Jun. 17-21, 2017, 23 pages.
Seleznev, N. et al., "Coherent Interpretation of Wideband Electromagnetic measurements in th emillihertz to Gigahertz Frequency Range", Petrophysics, 2018, 59(3), pp. 334-353.
Tian, L. et al., "A neutron-Induced Gamma-Ray Spectroscopy Logging Method for Determining Formation Water Salinity", SPWLA 60th Annual Logging Symposium, The Woodlands, TX, USA, 2019, 11 pages.

* cited by examiner

DETERMINATION OF FORMATION WATER SALINITY USING DOWNHOLE LOW FREQUENCY ELECTROMAGNETIC MEASUREMENTS AND PERMITTIVITY DISPERSIONS BASED THEREON

FIELD

The present disclosure relates to methods and systems that can determine formation water salinity and other useful formation properties (such as formation water saturation) based on the formation water salinity.

BACKGROUND

In oilfield applications, geological knowledge of subsurface formation rock is useful for resources exploration, field development and production planning. In shaly sand formations, the influence of clays contained in the formation rock can be determined by excess conductivity contribution. Quantifying shales has typically been limited to correlations with logs such as gamma ray (GR), sonic, or differences in the neutron and density logs. These correlations are based on fundamentally different physics than the controls on conductivity. This limits their applicability to the specific field where they are developed.

There has been considerable interest in applying dielectric measurements to determine oil saturation in shaly sands. Such oil saturation can be used to assess reservoir quality and the amount of hydrocarbons in-place in shaly sands. Formation conductivity and permittivity depend on formation water salinity as well as other formation properties such as water saturation, types and/or volumes of clay minerals and porosity. Having an in-depth understanding of these parameters is necessary to interpret dielectric measurements to determine oil saturation in shaly sands.

Different methods have been used to measure salinity of the formation water found within formation rock.

In one example, downhole fluid sampling methods can be used to obtain a sample of formation water. The sample can be analyzed by laboratory methods to measure the salinity of the formation water sample. The downhole fluid sampling requires that the formation water be mobile, i.e., in the transition zone or water leg.

In another example, it has been suggested that downhole NMR measurements can be used to understand changes to formation water salinity. See, for example, Clinch, S.; Shafer, S.; Wei, W.; Lasswell, P., "Determining Formation Water Salinity in the Hydrocarbon Leg using Cores and Logs," PETROPHYSICS, 52(2), 108-123, 2011.

In yet another example, pulsed neutron gamma spectral methods can be used to measure the salinity of formation water. See, for example, i) Ma., S. M.; Pfutzner, H.; AL-Hajiri, A. A.; et al., "Resolving the mixed salinity challenges with a methodology developed from pulsed neutron capture gamma ray spectral measurements", SPE 170608, Annual Technical Conference and Exhibition Society of Petroleum Engineers, 2014; ii) Ma, S. M., et al., "Formation water salinity from borehole measurements," U.S. Pat. No. 10,208,582, 19 Feb. 2019; iii) Pfutzner, H., et al., "Method for measuring formation water salinity from within a borehole," U.S. Pat. No. 10,247,849, 2 Apr. 2019; and iv) Tian, L.; Zhang, F.; Zhang, Q.; Chen, Q; Wang, X.; Qui, F. "A neutron-induced Gamma-Ray Spectroscopy Logging Method for Determining Formation Water Salinity," SPWLA 60th Annual Logging Symposium, The Woodlands, Tex., USA, Jun. 15-19, 2019.

In still another example, higher frequency (20 MHz to 1 GHz) dielectric data can be obtained and processed to measure the salinity of formation water. See, for example, Seleznev, N., Hou, C., Freed, D., Habashy, T., Feng, L. Fellah, K. and Xu, G., "Coherent interpretation of wideband electromagnetic measurements in the millihertz to gigahertz frequency range," SPWLA 58th Annual Logging Symposium, 2017. This method is not accurate if formation water salinity is low and high. Furthermore, if the measurement of the higher frequency (20 MHz to 1 GHz) dielectric data is shallow, it may not be representative of formation water salinity.

All of these methods can also be time consuming and costly.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with the subject disclosure, methods and systems are provided for measuring multifrequency permittivity data of a subsurface formation from downhole electromagnetic measurements at multiple frequencies below 1 MHz. The multifrequency permittivity data is processed to estimate salinity of the formation water of the subsurface formation. Other useful formation properties (such as formation water saturation) can be determined based on the estimate of salinity of the formation water. The downhole low frequency electromagnetic measurements are nondestructive, and the results indicate that the methods and systems are highly sensitive to the existence of clays.

In embodiments, the methods and systems can process the multifrequency permittivity data by calculating derivatives of the multifrequency permittivity data and using such derivatives to determine a slope representing change in permittivity relative to change in frequency. The slope can be used as an input to a first calibration equation that relates the slope to a calibration parameter. A value for the calibration parameter can be determined by solving the first calibration equation given the slope as input. The value of the calibration parameter can be used as input to a second calibration equation that relates the calibration parameter to salinity of the formation water of the subsurface formation. A value for the salinity of the formation water can be determined by solving the second calibration equation given the calibration parameter as input.

In embodiments, the multifrequency permittivity data and the underlying downhole electromagnetic measurements can involve a set of frequencies less than 1 MHz. In embodiments, the set of frequencies less than 1 MHz can possibly include frequencies between 1 MHz and 1 KHz and/or frequencies between 1 KHz and 100 Hz and/or frequencies between 100 Hz and 10 Hz.

In embodiments, the first calibration equation relates the slope and at least one additional parameter to the calibration parameter. For example, the at least one additional parameter can represent clay volume and possibly frequency.

In embodiments, the first calibration equation can have the form $$V_{clay} = a \frac{d\varepsilon}{df} f^b,$$

where $V_{clay}$ is clay volume, $$\frac{d\varepsilon}{df}$$

is the slope representing change in permittivity relative to change in frequency, f is frequency, and a and b are calibration parameters, where a is the calibration parameter determined by solving the first calibration equation.

In embodiments, the second calibration equation can have the form $Sal=C_1 \times a^2 + C_2 \times a + C_3$, where $C_1$, $C_2$ and $C_3$ are calibration constants, a is the calibration parameter determined by solving the first calibration equation and input to the second calibration equation, and Sal is a value of formation water salinity determined by solving the second calibration equation.

In embodiments, the second calibration equation can be selected from a set of calibration equations corresponding to different formation temperatures, where the selection is based on measured formation temperature of the subsurface formation.

In embodiments, either one or both of the first and second calibration equations can be selected from calibration equations corresponding to different clay volume and type, where the selection is based on a determination of clay volume and type of the subsurface formation. In embodiments, the clay volume can include single clay types such as kaolinite, smectite, illite, chlorite, and possibly combinations thereof.

In embodiment, the measurement of the multifrequency permittivity data and the processing of such data can be performed by a processor. The operations of the method or system or parts thereof can also be controlled by a processor.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein:

FIGS. 2A, 2B and 2C depict plots of relative permittivity computed as a function of frequency (in Hz) for a shaly sand formation rock containing different clay volumes (including 1%, 5%, 10%, 20% and 30%) with a water volume of 24% and different formation water salinities of 30 ppk (FIG. 2A), 60 ppk (FIG. 2B) and 150 ppk (FIG. 2C).

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Hydrocarbon-bearing subsurface formation rock such as shaly sands can contain different types of clays and different amounts of such clay types. Each clay type has its own different characteristics, which can be translated to what is called cation exchange capacity (CEC) in common petrophysical applications. Clays are hydrous aluminum silicate minerals that are platy in structure and can form by the alteration of silicate minerals like feldspar and amphibole. Clays are commonly lumped or grouped into a number of clay types, including but not limited to smectite, kaolinite, chlorite, illite. Some clays have a tendency to swell when exposed to water, creating a potential drilling hazard when clay-bearing formation rock is exposed to water-based fluids during drilling, possibly reducing the permeability of the reservoir rock. Clays can also reduce the permeability of reservoir rock when clay-bearing formation rock is exposed to water-based stimulation fluids. The structural differences amongst the clay types (smectite, kaolinite, chlorite, illite) can determine the surface area exposed to reservoir fluids or drilling fluids or stimulating fluids. Clays can be found in pore spaces, as part of the matrix or as grain-cementing material. Authigenic clays, which grow in the pores from minerals in the connate water, can be pore-filling or pore-lining. These clays have considerable surface area exposed in the pore and can be reactive, while detrital clays that are part of the matrix are usually less reactive. Additionally, clays can be cementing, or grain-binding, materials that react with water or acid to disaggregate the formation if they are not protected by quartz overgrowths. The most common clays that create clay problems in hydrocarbon reservoirs are kaolinite, smectite, illite and chlorite.

Interfacial polarization can be observed in formation rock containing clays (such as shaly sands) and in other porous media containing clays. When the surface of a nonconductive mineral, such as clay minerals and silica grains, are exposed to electrolytes, it acquires charges due to ionic adsorption, protonation/deprotonation of the hydroxyl groups, and dissociation of other potentially active surface groups. In the presence of an external electromagnetic (EM) field, these surface charges form electric dipoles and cause interfacial polarization (IP) effects. The strength of the IP effects is regulated by permittivity of the formation rock or other porous media.

At lower frequencies (below 1 MHz), the permittivity of porous media shows strong dispersions due to existence of clays, and such dispersions mostly depend on formation water salinity and clay volumes.

The present disclosure provides a methodology or framework that uses low frequency (below 1 MHz) downhole electromagnetic measurements of a subsurface formation to determine multifrequency permittivity (referred to herein as a "permittivity dispersion") of the subsurface formation over a range of low frequencies (below 1 MHz). The permittivity dispersion of the subsurface formation is processed to determine or quantify salinity of formation water contained in the subsurface formation. Other useful formation properties (such as formation water saturation) can be determined based on the formation water salinity.

In a shaly sands environment, formation permittivity depends mainly on the following parameters: formation water volume (which is dependent on formation porosity and water saturation); formation water salinity; clay types and clay volumes for the formation rock; and grain size and shapes for the formation rock.

A mathematic model can be used to calculate formation permittivity based on the above listed parameters. The model calculates formation complex conductivity by analyzing the EM response of a representative volume comprising a single, isolated electrically conductive inclusion (such as clay grains) surrounded by the host material (such as water). The effective medium theory was applied to formulate the model. The outputs of the mathematical model include formation conductivity and formation permittivity, which are parts of the complex formation conductivity ($\sigma$) given as:

$$\sigma = \sigma^R + i\omega\varepsilon_0\varepsilon_r \quad \text{Eqn. (1)}$$

where $\sigma^R$ is the in-phase component of the complex formation conductivity; and $\omega\varepsilon_0\varepsilon_r$ is the quadrature component of the complex formation conductivity with w representing frequency, $\varepsilon_0$ representing permittivity of vacuum (8.854× $10^{-12}$) and $\varepsilon_r$ representing relative permittivity.

For a porous media containing clay minerals, $\varepsilon_r$ depends on water volume, water salinity, clay volumes and grain size and shape. Both $\sigma^R$ and $\varepsilon_r$ can be calculated from the mathematical model.

Figure 1A:
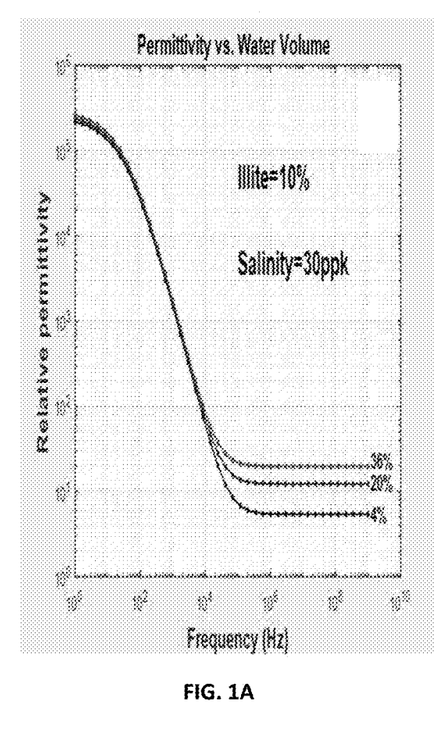
FIGS. 1A, 1B and 1C depict plots of relative permittivity computed as a function of frequency (in Hz) for a shaly sand formation rock containing 10% illite under different water volumes (including 4%, 20% and 36%) and different formation water salinities of 30 ppk (FIG. 1A), 60 ppk (FIG. 1B) and 150 ppk (FIG. 1C)
Figure 1B:
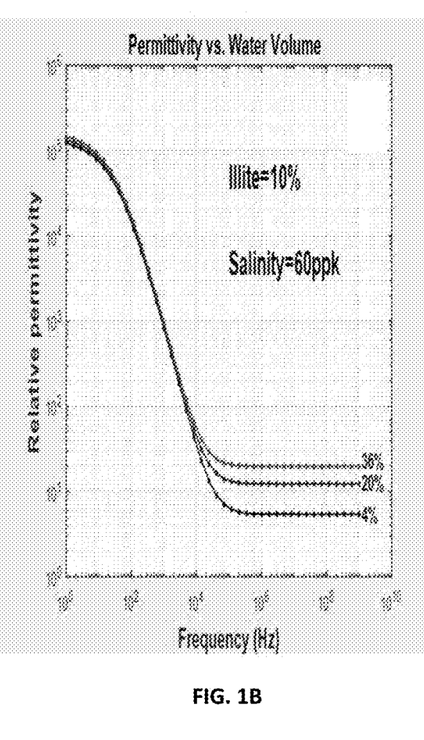
Figure 1C:
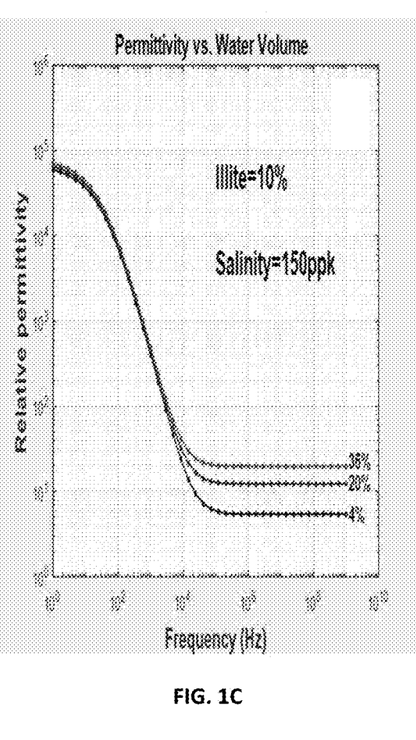

FIGS. 1A, 1B and 1C show calculations of relative permittivity $\varepsilon_r$ as a function of frequency $\omega$ (in Hz) for a shaly sand matrix under different water volumes of 4%, 20% and 36%. The shaly sand matrix of the three examples includes 90% sandstone and 10% illite assuming spherical grains. Three different water salinities are used in the calculations. Specifically, the calculations of FIG. 1A employ a water salinity of 30 parts per thousand (ppk), the calculations of FIG. 1B employ a water salinity of 60 parts per thousand (ppk), and the calculations of FIG. 1C employ a water salinity of 150 parts per thousand (ppk). Based on the plots, the characteristics of the relative permittivity $\varepsilon_r$ as a function of frequency $\omega$ (in Hz) can be summarized as follows: strong dispersions in relative permittivity below 10 kHz; the dispersions in relative permittivity do not depend on water volume; the relative permittivity decreases with the increased water salinity; and above 100 kHz, there is no dispersion and the relative permittivity depends on water volume.

Figure 2A:
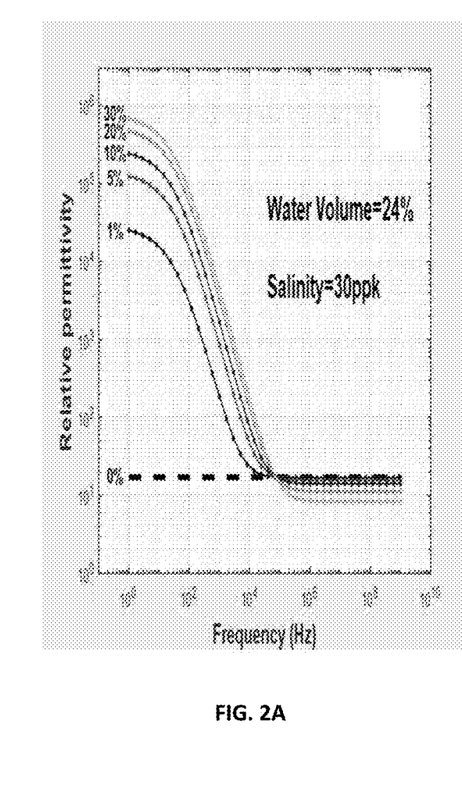
FIGS. 2A, 2B and 2C also include horizontal dashed lines depicting relative permittivity computed as a function of frequency (in Hz) for a clay-free shaly sand formation rock (0% clay) with a water volume of 24% and different formation water salinities of 30 ppk (FIG. 2A), 60 ppk (FIG. 2B) and 150 ppk (FIG. 2C)
Figure 2B:
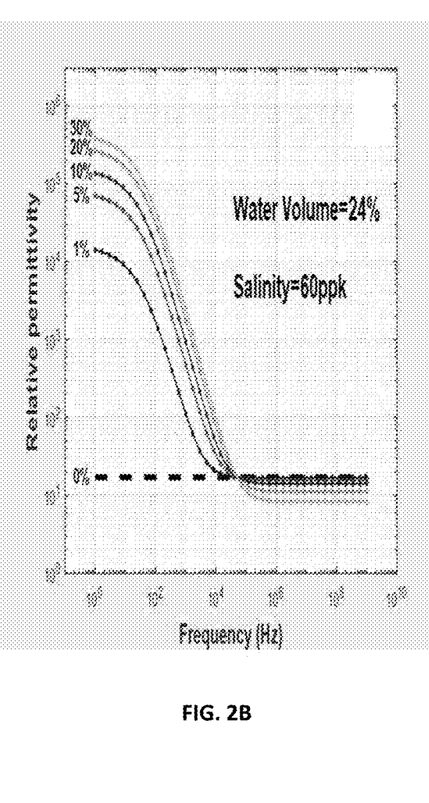
Figure 2C:
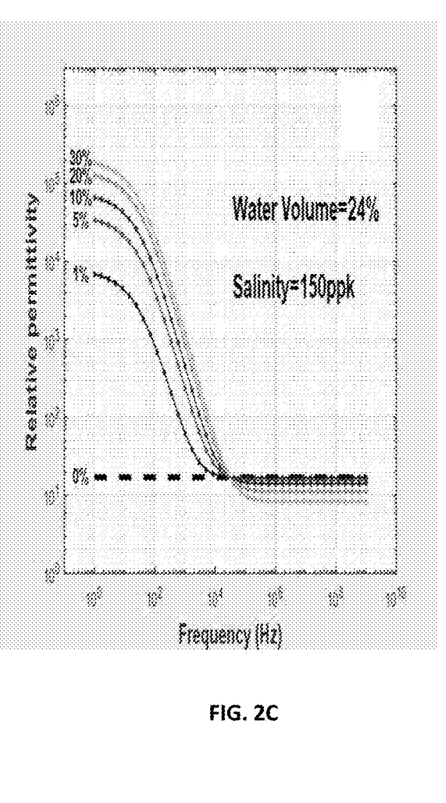

Clearly, the permittivity dispersions at the low frequency range do not depend on water volume. On the other hand, the same permittivity dispersion curves strongly depend on clay volume, as depicted in FIGS. 2A, 2B and 2C. Specifically, the curves of FIGS. 2A, 2B and 2C show relative permittivity $\varepsilon_r$ as a function of frequency $\omega$ (in Hz) for different clay volumes of 1%, 5%, 10%, 20%, and 30% respectively. For comparison, the relative permittivity $\varepsilon_r$ as a function of frequency $\omega$ (in Hz) for clean sandstone (0% clay volume) is also plotted as a horizontal dashed line in FIGS. 2A, 2B and 2C. The permittivity dispersion curves of FIGS. 2A, 2B and 2C are derived from variations in water salinity of 30 parts per thousand (ppk), 60 parts per thousand (ppk) and 150 parts per thousand (ppk), respectively, which is similar to the curves of FIGS. 1A, 1B and 1C. Furthermore, all of the permittivity dispersion curves of FIGS. 2A, 2B and 2C are derived from a water volume (product of water saturation and porosity) of 24%. It can be observed that while the clean sandstone has no dispersion, the shaly sands show strong dispersion effects. Even with 1% clay volume, the dispersion curve shows a large difference from the clean sands, indicating that it is very sensitive to clay volume. In addition, the amplitude of the dispersion depends on water salinity. The higher the water salinity, the lower the amplitude of dispersion.

Figure 3A:
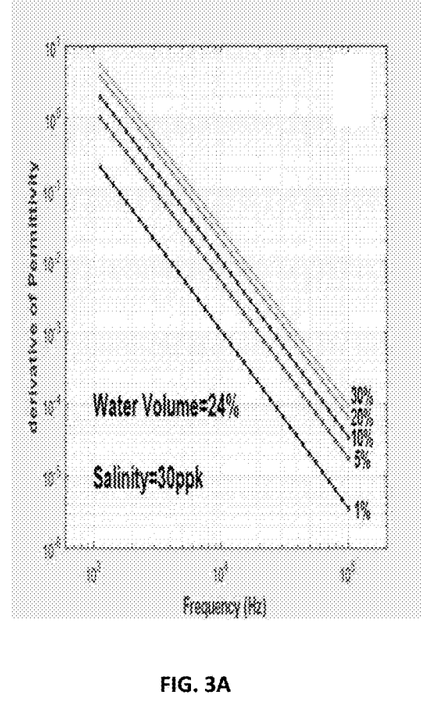
FIGS. 3A, 3B and 3C depict plots of the derivatives of the relative permittivity as a function of frequency (in Hz) of FIGS. 2A, 2B and 2C for the shaly sand formation rock containing different clay volumes (including 1%, 5%, 10%, 20% and 30%) with a water volume of 24% and different formation water salinities of 30 ppk (FIG. 3A), 60 ppk (FIG. 3B) and 150 ppk (FIG. 3C)
Figure 3B:
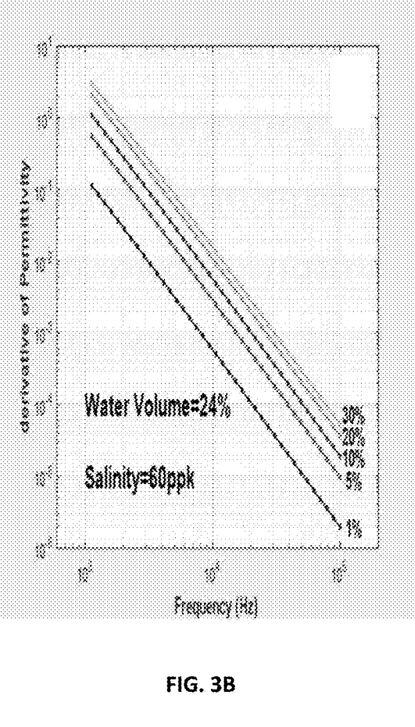
Figure 3C:
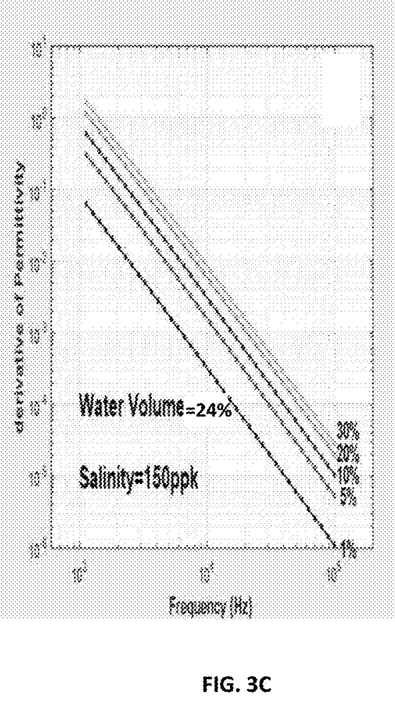

The permittivity dispersion curves from the different clay volumes have different slopes, which can be used for quantifying clay volumes. FIGS. 3A, 3B and 3C show the derivatives of relative permittivity $\varepsilon_r$ as a function of frequency for the corresponding curves in FIGS. 2A, 2B and 2C. As expected, each clay volume has a unique, but different derivative. Carefully examining all the derivative curves of FIGS. 3A, 3B and 3C, an empirical formula can be defined as:

$$V_{clay} = a\frac{d\varepsilon}{df}f^b, \quad \text{Eqn. (2)}$$

where $V_{clay}$ is clay volume, $$\frac{d\varepsilon}{df}$$

is the slope of the curve representing change in relative permittivity $\varepsilon_r$ as a function of change in frequency, f is frequency, and a and b are calibration parameters.

Formation pressure and formation temperature are two additional factors that can be considered when calculating relative permittivity and its derivative. Through simulations it was determined that formation pressure has little effect on relative permittivity and can be eliminated from further considerations. Formation temperature, however, can impact water conductivity, charge density at the surface of clay grains and, therefore, affect relative permittivity and its derivatives. The temperature effects can be simulated and corrected as will be demonstrated below.

Figure 4:
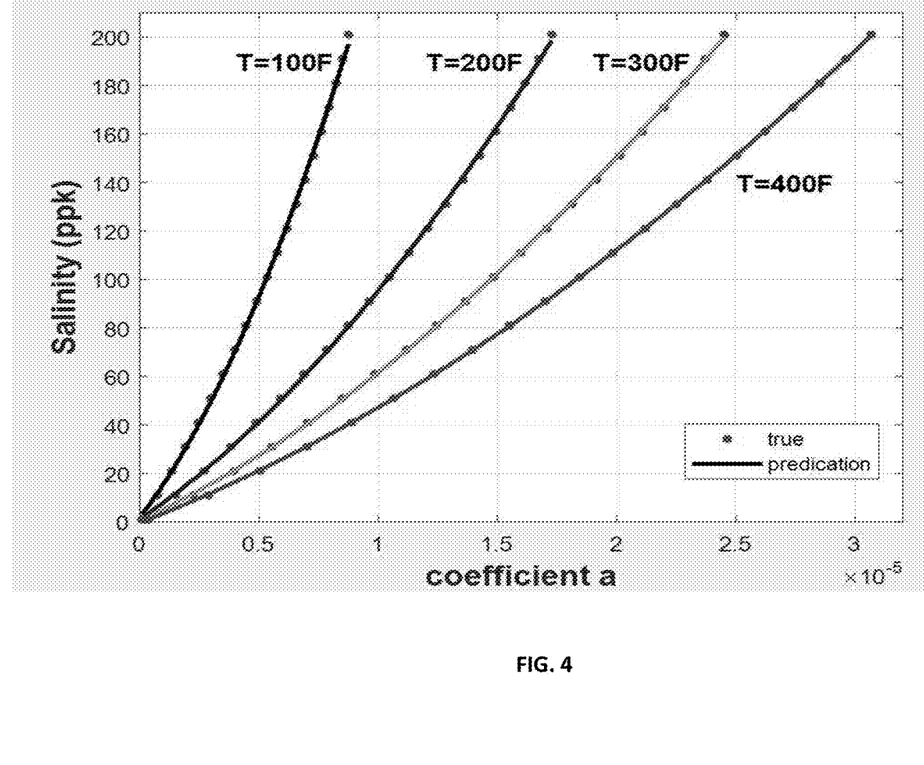
FIG. 4 depicts correlation curves between the calibration parameter a of the calibration equation (1) as described herein to formation water salinity (in ppk) for four different formation temperatures of 100° F., 200° F., 300° F., and 400° F.

Based on model simulations, it was found that the calibration parameter b of Eqn. (2) can be defined as a constant value (preferably 2.45). Furthermore, the calibration parameter a of Eqn. (2) can be defined by a correlation with formation water salinity for a known temperature as depicted in FIG. 4. The non-linear dependence between the calibration parameter a and formation water salinity allows for calculation of formation water salinity (Sal) from the knowledge of the value of the calibration parameter a of Eqn. (2) according to the following:

$$Sal = C_1 \times a^2 + C_2 \times a + C_3 \qquad \text{Eqn. (3)}$$

where $C_1$, $C_2$ and $C_3$ are calibration constants.

In embodiments, the formation water salinity (Sal) can be expressed in a dimensionless unit such as parts per kilo or thousand (ppk), parts per million (ppm), fractional percentage, or another suitable unit. The formation water salinity (Sal) represents the relative amount of salt dissolved in the formation water.

In embodiments, the calibration parameter a of Eqn. (2) can be dependent on both clay type and clay volume. Thus, in application, knowledge of clay type and clay volume from other logs or other historical data can be used in Eqn. (2) to determine the calibration parameter a, which is then used as part of Eqn. (3) to determine salinity of the formation water.

As an application, multifrequency permittivity data of a subsurface formation can be measured from downhole electromagnetic measurements at frequencies below 1 MHz of the formation of the interest. Derivatives can be calculated from the measured multifrequency permittivity data. Clay type and clay volume $V_{clay}$ can be determined from analysis of rock cores, drill cuttings and/or logs (such as element spectroscope surveys). The calibration parameter b can be assumed to be a constant for the clay volume and type. Derivatives can be calculated from the measured multifrequency permittivity data and used to determine the slope $$\frac{d\varepsilon}{df}.$$

Eqn. (2) can be used to solve for the calibration parameter a. Then, with temperature of subsurface formation determined by logging or other measurements, the appropriate calibration of Eqn. (3) corresponding to the formation temperature and clay volume and type can be used to calculate a value of salinity (Sal) of formation water for the subsurface formation.

The following observations can be based on FIGS. 1A-1C, 2A-2C, 3A-3C and 4:
(a) the permittivity dispersion curves for shaly sands at low frequencies below 1 MHz do not depend on water volume. This makes the permittivity dispersion curve an ideal clay detector for all saturation conditions, pay zones or otherwise;
(b) the permittivity dispersion curves for shaly sands strongly depend on clay type and volume. Even with 1% clay volume, the permittivity dispersion curves show a huge difference from the one with clean sand;
(c) the derivatives of the dispersion curves have a well-defined correlation with clay type and clay volume. The correlation can be modeled by an empirical formula shown in Eqn. (2);
(d) there are two calibration parameters a and b. In embodiments, the calibration parameter b can be a constant value (e.g. 2.45) while the calibration parameter a has a well-defined correlation with water salinity; and
(e) formation water salinity can be estimated based on calculation of the calibration parameter a and formation temperature using Eqn. (3).

To use the permittivity measurements for practical applications, the permittivity dispersion data of the subsurface formation can be measured from downhole electromagnetic measurements at multiple frequencies below 1 MHz. The derivatives of the permittivity dispersion data can be used to estimate salinity of the formation water. Other useful formation properties (such as formation water saturation) can be determined based on the estimate of salinity of the formation water.

Figure 5:
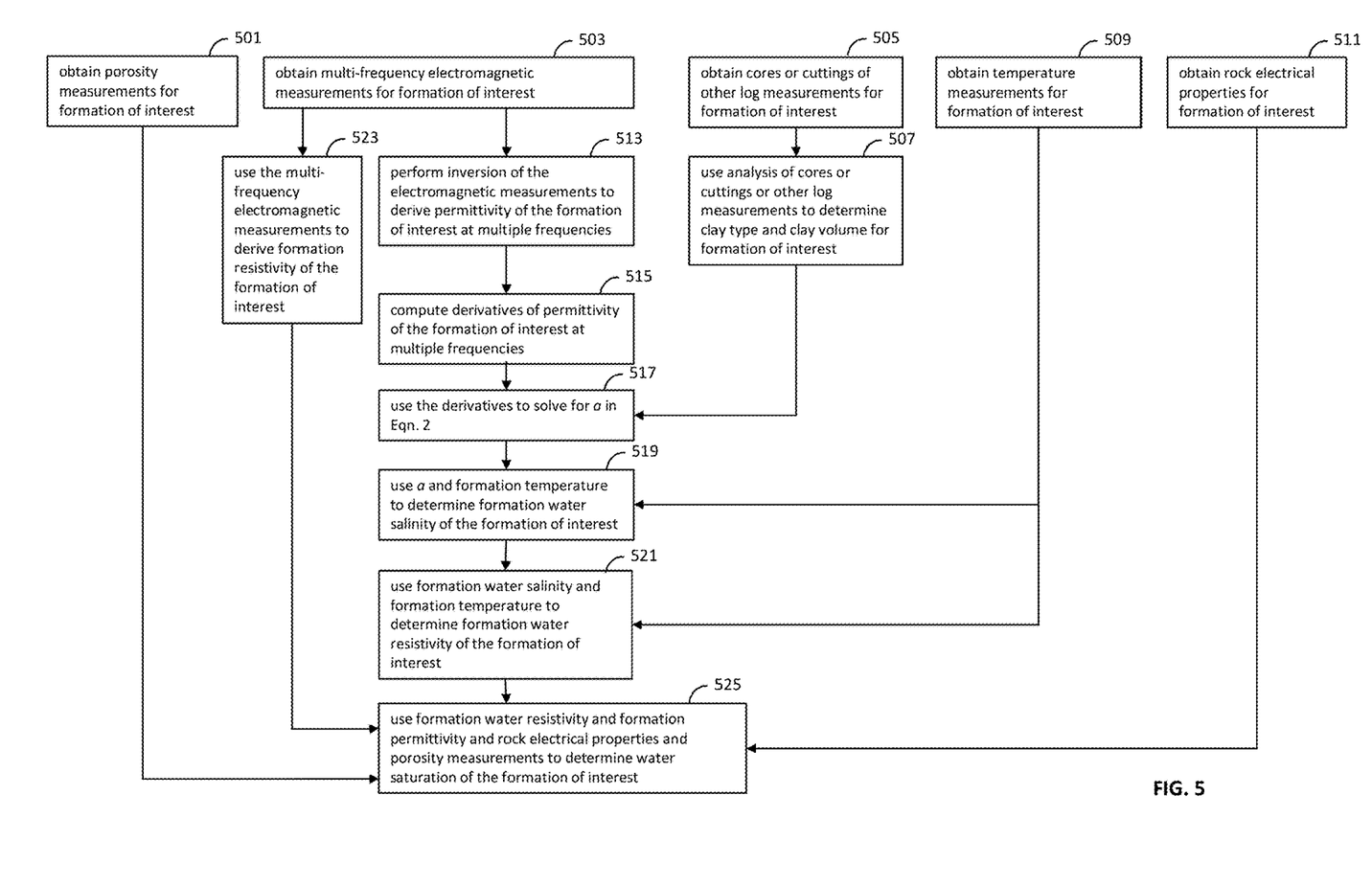
FIG. 5 is a flowchart illustrating a methodology for measuring multifrequency permittivity data of a subsurface formation from downhole electromagnetic measurements. The multifrequency permittivity data is processed to estimate salinity of the formation water of the subsurface formation. Other useful formation properties (such as formation water saturation) can be determined based on the estimate of salinity of the formation water.

FIG. 5 depicts a workflow that uses downhole electromagnetic measurements at frequencies below 1 MHz of a subsurface formation of interest to determine multifrequency permittivity data (or permittivity dispersion data) for the formation of interest over a range of low frequencies (below 1 MHz). The multifrequency permittivity data of the subsurface formation of interest is processed to determine or quantify salinity of formation water contained in the subsurface formation of interest. Other useful formation properties (such as formation water saturation) can be determined based on the formation water salinity.

In block 501, porosity measurements of the formation of interest are obtained. In embodiments, the porosity measurements can be performed by one or more downhole tools (such as a gamma-ray density tool, neutron density tool, or NMR tool) that are located in a desired depth location in a borehole that traverses the formation of interest and/or possibly by laboratory analysis of one or more core samples collected from the formation of interest.

In block 503, multifrequency electromagnetic measurements of the formation of interest are obtained. In embodiments, the electromagnetic measurements can be performed by a downhole EM logging tool (which can part of a wireline logging tool, a logging-while-drilling logging tool, a measurement-while-drilling logging tool, or a tripping-while-drilling logging tool). The electromagnetic measurements can be dispersed at low frequencies (below 1 MHz). In block 503, the downhole EM logging tool can be located in a desired depth location in a borehole that traverses the formation of interest and operated to measure complex conductivity data representing conductivity of the formation of interest at the multiple low frequencies less than 1 MHz. In embodiments, the multiple low frequencies less than 1 MHz can possibly include frequencies between 1 MHz and 1 KHz and/or frequencies between 1 KHz and 100 Hz and/or frequencies between 100 Hz and 10 Hz. For each one of the multiple low frequencies of the experiment, the frequency of the applied time varying external electromagnetic field produced by the transmitter antenna of the downhole EM logging tool can be controlled to correspond to the particular low frequency, and the electromagnetic response of the formation of interest can be measured by the downhole EM logging tool for that particular low frequency.

In block 505, rock core sample(s) or cuttings of other log measurements are obtained for the formation of interest. In block 507, the rock core(s) or cuttings or other log measurements of 505 are analyzed to determine clay type and clay volume for the formation of interest.

In block 509, temperature measurements are obtained to determine formation temperature for the formation of interest. In embodiments, the temperature measurements can involve measuring borehole temperature or the temperature of core samples or fluid samples collected from the formation of interest.

In block 511, rock electrical properties are obtained for the formation of interest. In embodiments, formation resistivity is obtained using electromagnetic tool such as array induction tool (AIT) of Schlumberger.

In block 513, operations perform an inversion of the electromagnetic measurements of block 503 for each frequency within a set of frequencies below 1 MHz to derive relative permittivity of the formation of interest at the multiple frequencies. For example, an induction logging tool as set forth in U.S. Pat. No. 7,501,829 can be used to obtain the multifrequency electromagnetic measurements of block 503. By recording and processing the receiver voltage signal sensed by the receiver coils of the induction logging tool for each frequency within the set of frequencies below 1 MHz, measurements of complex conductivity of the formation of interest can be obtained for three different radial depths (shallow/medium, deep) into the formation for each one of the multiple frequencies. The relative permittivity of the formation of interest at the respective depth locations (shallow, medium, deeper) and corresponding frequency can be extracted from the quadrature component of the complex conductivity measurements obtained by the induction logging tool.

In block 515, operations compute derivatives of the relative permittivity of the formation of interest as a function of frequency at the multiple frequencies as derived in block 513.

In block 517, operations use the derivatives of the relative permittivity of the formation of interest as a function of frequency as computed in block 515 to solve for the calibration parameter a of Eqn. (2). In embodiments, the clay volume as determined in block 505 and the calibration parameter b (which is assumed to be a constant) are used as inputs to Eqn. (2). Furthermore, the derivatives calculated from the measured multifrequency permittivity data can also be used to determine a slope $$\frac{d\varepsilon}{df}$$

for input to Eqn. (2).

In block 519, operations use the parameter a solved for in block 517 and the formation temperature of block 509 to determine formation water salinity (Sal) of the formation of interest. In embodiments, with temperature of formation of interest determined in block 509, the appropriate calibration equation of the form of Eqn. (3) corresponding to the formation temperature can be used to calculate a value of salinity (Sal) of formation water for the formation of interest. In embodiments, the parameter a solved for in block 517 can be used as input to the appropriate calibration equation of the form of Eqn. (3) that corresponds to the formation temperature. Data representing the formation water salinity (Sal) of the formation of interest can be stored in electronic memory or output therefrom as needed (such as block 521).

In block 521, operations use the formation water salinity of block 519 and the formation temperature of block 509 to determine formation water resistivity of the formation of interest. This can be accomplished using published charts such as The Schlumberger log interpretation chartbook. Data representing the formation water resistivity of the formation of interest can be stored in electronic memory or output therefrom as needed (such as block 525).

In block 523, operations use the multifrequency electromagnetic measurements of block 503 to derive formation resistivity of the formation of interest. This can be accomplished using a multifrequency dielectric scanner, such as the array dielectric tool (ADT), of Schlumberger. Data representing the formation resistivity of the formation of interest can be stored in electronic memory or output therefrom as needed (such as block 525).

In block 525, operations use the formation water resistivity of block 521 and the formation resistivity of block 523 and the rock electrical properties of block 511 and the formation porosity measurements of block 501 to determine water saturation of the formation of interest. Such operations can use the well-known Archie equation or the modified Archie equation such as Dual-water or Waxman-Smith models, which calculates oil saturation and water saturation based on the total formation porosity. Data representing the formation water saturation of the formation of interest can be stored in electronic memory or output therefrom as needed.

In embodiments, the operations of the workflow of FIG. 5 can be performed over different depth intervals within a borehole that traverses the subsurface formation of interest in order to determine or quantify salinity of formation water over the depth intervals of the formation of interest. Other useful formation properties (such as formation water saturation) water over the depth intervals of the formation of interest can be determined based on the formation water salinity over the depth intervals of the formation of interest.

Figure 6:
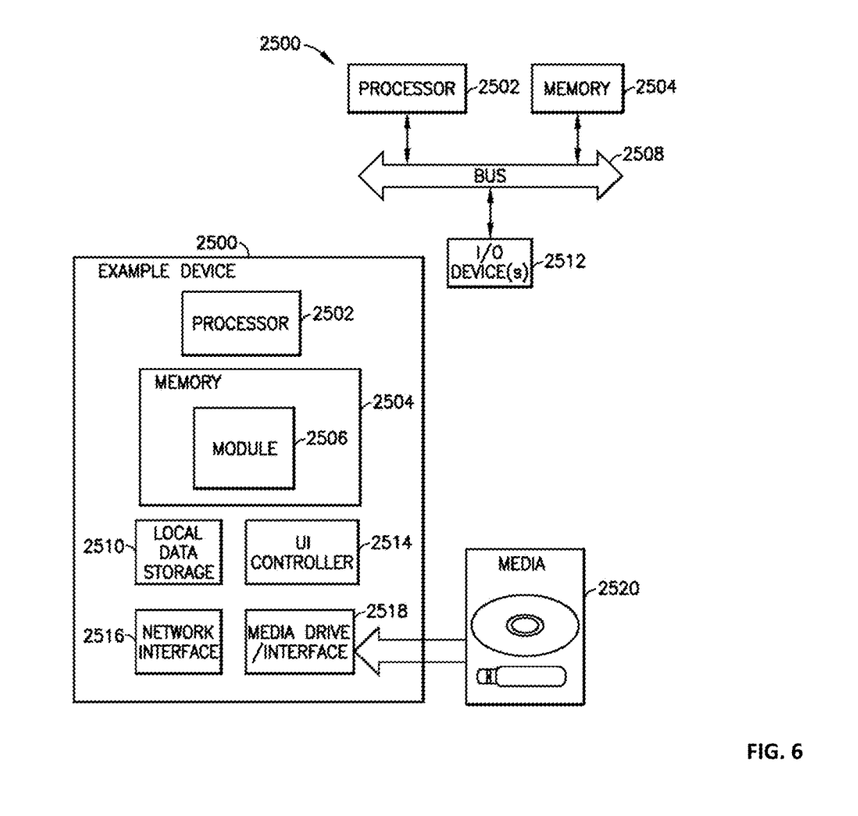
FIG. 6 is a block diagram of a computer processing system, which can be used to embody parts of the methodology for quantification of formation water salinity and other useful formation properties based thereon.

FIG. 6 illustrates an example device 2500, with a processor 2502 and memory 2504 that can be configured to implement various embodiments of the methods and workflows as discussed in this disclosure. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more of computers, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network.

A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user (such as a human annotator) to enter commands and information to device 2500 and allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various processes of present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer. Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general-purpose computer) for executing any of the methods and processes described above.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively, or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members.

Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

There have been described and illustrated herein several embodiments of methods and systems for measuring permittivity dispersion data of a subsurface formation from downhole electromagnetic measurements at multiple frequencies below 1 MHz and estimating salinity of the formation water of the subsurface formation. Other useful formation properties (such as formation water saturation) can be determined based on the estimate of salinity of the formation water. It will therefore be appreciated by those skilled in the art that yet other modifications could be made to the provided invention without deviating from its spirit and scope as claimed.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method for characterizing a subsurface formation, comprising:
    i) configuring and operating a downhole logging tool to conduct downhole electromagnetic measurements on the subsurface formation over a range of frequencies, and obtaining with the downhole logging tool the electromagnetic measurements, wherein the downhole electromagnetic measurements are used to determine and store multifrequency permittivity data that characterizes permittivity of the subsurface formation over a set of frequencies less than 1 MHz;
    ii) processing the multifrequency permittivity data to determine salinity of formation water of the subsurface formation, wherein the processing of ii) involves:
    calculating derivatives of the multifrequency permittivity data;
    using such derivatives to determine a slope representing change in permittivity relative to change in frequency;
    using the slope as an input to a first calibration equation that relates the slope to a calibration parameter, wherein a value for the calibration parameter is determined by solving the first calibration equation given the slope as input; and
    using the value of the calibration parameter as input to a second calibration equation that relates the calibration parameter to salinity of the formation water of the subsurface formation, wherein a value for the salinity of the formation water is determined by solving the second calibration equation given the calibration parameter as input; and
    (iii) using the salinity of formation water of the subsurface formation to determine at least one of a field development plan for the subsurface formation and a production plan for the subsurface formation.

2. A method according to claim 1, further comprising:
storing or outputting data that represents the salinity of the formation water of the subsurface formation.

3. A method according to claim 1, wherein:
the set of frequencies includes frequencies between 1 MHz and 1 KHz; and/or
the set of frequencies includes frequencies between 1 KHz and 100 Hz; and/or
the set of frequencies includes frequencies between 100 Hz and 10 Hz.

4. A method according to claim 1, further comprising:
determining at least one additional formation property based on the salinity of the formation water of the subsurface formation.

5. A method according to claim 4, wherein:
the at least one additional formation property comprises formation water saturation.

6. A method according to claim 1, wherein:
the first calibration equation relates the slope and at least one additional parameter to the calibration parameter.

7. A method according to claim 1, wherein:
the at least one additional parameter represents at least one of clay volume and frequency.

8. A method according to claim 1, wherein:
the first calibration equation has the form $$V_{clay} = a \frac{d\varepsilon}{df} f^b,$$

where $V_{clay}$ is clay volume, $$\frac{d\varepsilon}{df}$$

is the slope representing change in permittivity relative to change in frequency, f is frequency, a and b are calibration parameters, where a is the calibration parameter determined by solving the first calibration equation.

9. A method according to claim 1, wherein:
the second calibration equation has the form $Sal=C_1 \times a^2 + C_2 \times a + C_3$, where $C_1$, $C_2$ and $C_3$ are calibration constants, a is the calibration parameter determined by solving the first calibration equation and input to the second calibration equation, and Sal is a value of salinity of formation water determined by solving the second calibration equation.

10. A method according to claim 1, wherein:
the second calibration equation is selected from a set of calibration equations corresponding to different formation temperatures, where the selection is based on measured formation temperature of the subsurface formation.

11. A method according to claim 1, wherein:
at least one of the first and second calibration equations are selected from calibration equations corresponding to different clay volume and clay type, where the selection is based on a determination of clay volume and clay type of the subsurface formation.

12. A method according to claim 11, wherein:
the clay types include kaolinite, smectite, illite, chlorite, and possibly combinations thereof.

13. A method according to claim 1, wherein:
the processing of ii) is performed by a processor.

14. A method according to claim 1, wherein the salinity of formation water of the subsurface formation is used to determine the field development plan for the subsurface formation.

15. A method according to claim 1, wherein the salinity of formation water of the subsurface formation is used to determine the production plan for the subsurface formation.

16. A method according to claim 1, wherein the salinity of formation water of the subsurface formation is used to determine the field development plan and the production plan for the subsurface formation.

17. A method for characterizing a subsurface formation, comprising:
  i) obtaining multifrequency permittivity data that characterizes permittivity of the subsurface formation over a set of frequencies less than 1 MHz with a processor;
  ii) processing the multifrequency permittivity data with the processor to determine salinity of formation water of the subsurface formation, wherein the processing of ii) involves:
    calculating derivatives of the multifrequency permittivity data;
    using such derivatives to determine a slope representing change in permittivity relative to change in frequency;
    using the slope as an input to a first calibration equation that relates the slope to a calibration parameter, wherein a value for the calibration parameter is determined by solving the first calibration equation given the slope as input; and
    using the value of the calibration parameter as input to a second calibration equation that relates the calibration parameter to salinity of the formation water of the subsurface formation, wherein a value for the salinity of the formation water is determined by solving the second calibration equation given the calibration parameter as input; and
  (iii) using the salinity of formation water of the subsurface formation to determine at least one of a field development plan for the subsurface formation and a production plan for the subsurface formation.

18. A method according to claim 17, wherein:
the set of frequencies includes frequencies between 1 MHz and 1 KHz; and/or
the set of frequencies includes frequencies between 1 KHz and 100 Hz; and/or
the set of frequencies includes frequencies between 100 Hz and 10 Hz.

19. A method according to claim 17, wherein:
the at least one processor is further configured to determine at least one additional formation property based on the salinity of the formation water of the subsurface formation.

20. A method according to claim 17, wherein:
the multifrequency permittivity data is derived from multifrequency electromagnetic measurements performed by a downhole logging tool selected from the group consisting of a wireline logging tool, a logging-while-drilling logging tool, a measurement-while-drilling logging tool, and a tripping-while-drilling logging tool.

* * * * *